United States Patent
Kovac et al.

(10) Patent No.: US 6,200,134 B1
(45) Date of Patent: Mar. 13, 2001

(54) APPARATUS AND METHOD FOR CURING MATERIALS WITH RADIATION

(75) Inventors: Jozef Kovac, Danbury; Raymond L. Knox, Bethel, both of CT (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/009,205

(22) Filed: Jan. 20, 1998

(51) Int. Cl.$^7$ ....................................................... A61C 3/00
(52) U.S. Cl. ........................... 433/29; 433/215; 606/113; 362/800
(58) Field of Search ........................ 433/29, 215; 606/1, 606/13, 16; 607/88; 362/800

(56) References Cited

U.S. PATENT DOCUMENTS

| | | |
|---|---|---|
| 3,712,984 | 1/1973 | Lienhard . |
| 3,868,513 | 2/1975 | Gonser . |
| 3,970,856 | 7/1976 | Mahaffey et al. . |
| 4,185,891 * | 1/1980 | Kaestner ............................. 350/167 |
| 4,186,748 | 2/1980 | Schlager . |
| 4,298,806 | 11/1981 | Herold . |
| 4,450,139 | 5/1984 | Bussiere et al. . |
| 4,935,665 * | 6/1990 | Murata . |
| 4,936,808 * | 6/1990 | Lee . |
| 4,999,310 * | 3/1991 | Kim . |
| 5,029,957 | 7/1991 | Hood . |
| 5,115,761 | 5/1992 | Hood . |
| 5,162,696 * | 11/1992 | Goodrich . |
| 5,233,283 | 8/1993 | Kennedy . |
| 5,242,602 | 9/1993 | Richardson et al. . |
| 5,265,792 * | 11/1993 | Harrah et al. . |
| 5,278,629 | 1/1994 | Schlager et al. . |
| 5,283,425 * | 2/1994 | Imamura . |
| 5,312,249 | 5/1994 | Kennedy . |
| 5,316,473 | 5/1994 | Hare . |
| 5,373,114 * | 12/1994 | Kondo et al. . |
| 5,420,768 | 5/1995 | Kennedy . |
| 5,471,129 | 11/1995 | Mann . |
| 5,521,392 * | 5/1996 | Kennedy et al. . |
| 5,535,230 * | 7/1996 | Abe . |
| 5,617,492 * | 4/1997 | Beach et al. ............................. 385/33 |
| 5,634,711 | 6/1997 | Kennedy et al. . |
| 5,660,461 * | 8/1997 | Ignatius et al. . |
| 5,664,042 | 9/1997 | Kennedy . |
| 5,698,866 * | 12/1997 | Doiron et al. . |
| 5,707,139 * | 1/1998 | Haitz . |
| 5,711,665 | 1/1998 | Adam et al. . |
| 5,747,363 * | 5/1998 | Wei et al. . |

FOREIGN PATENT DOCUMENTS

| | | |
|---|---|---|
| 0116405 | 8/1984 | (EP) . |
| 830850 | 3/1998 | (EP) . |
| 2329756 * | 3/1999 | (GB) . |
| 6-30275 | 9/1995 | (JP) . |
| 8-141001 | 6/1996 | (JP) . |
| 9-10238 | 1/1997 | (JP) . |
| 8-194786 | 2/1997 | (JP) . |

OTHER PUBLICATIONS

Schlager, Kenneth J., Ignatius, Ronald W., *An LED–Array Light Source for Medical Therapy*, SPIE vol. 1892 Medical Lasers and Systems II (1993) p. 26–35.

* cited by examiner

Primary Examiner—Ralph A. Lewis
(74) Attorney, Agent, or Firm—Wood, Herron & Evans L.L.P.

(57) ABSTRACT

A hand held dental instrument for curing light-curable compounds comprises a housing and an array of solid state, light emitting junctions or dies for generating light having wavelengths within a narrow band of wavelengths (e.g. 400–500 nm). Preferably, a peak wavelength of 470 nm is generated. The device further comprises an optical fiber light pipe for capturing the light and transmitting a beam of the light to a work surface containing a light-curable compound. An optical lens or lenses may be used for focusing the light into the light pipe.

24 Claims, 3 Drawing Sheets

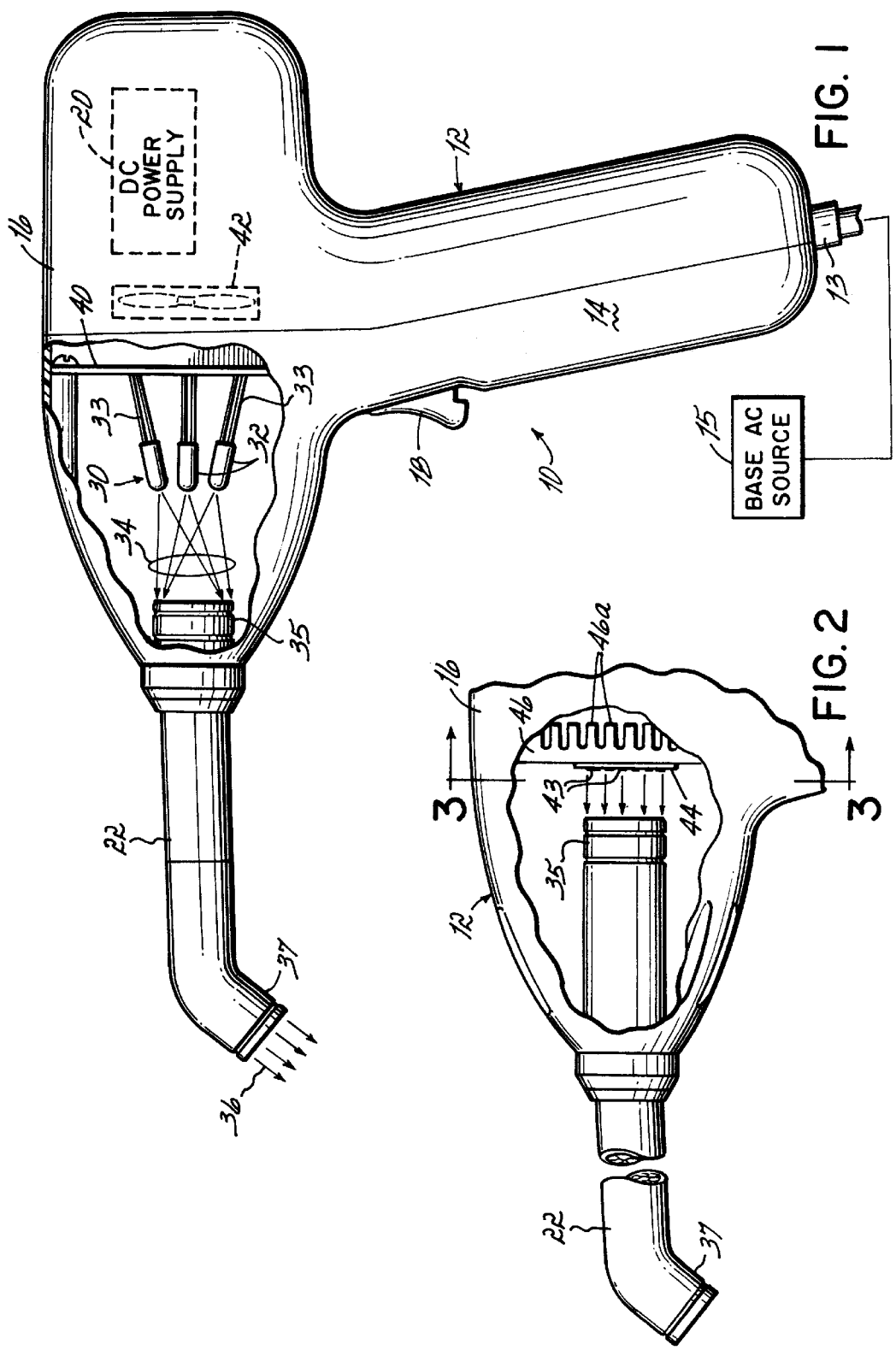

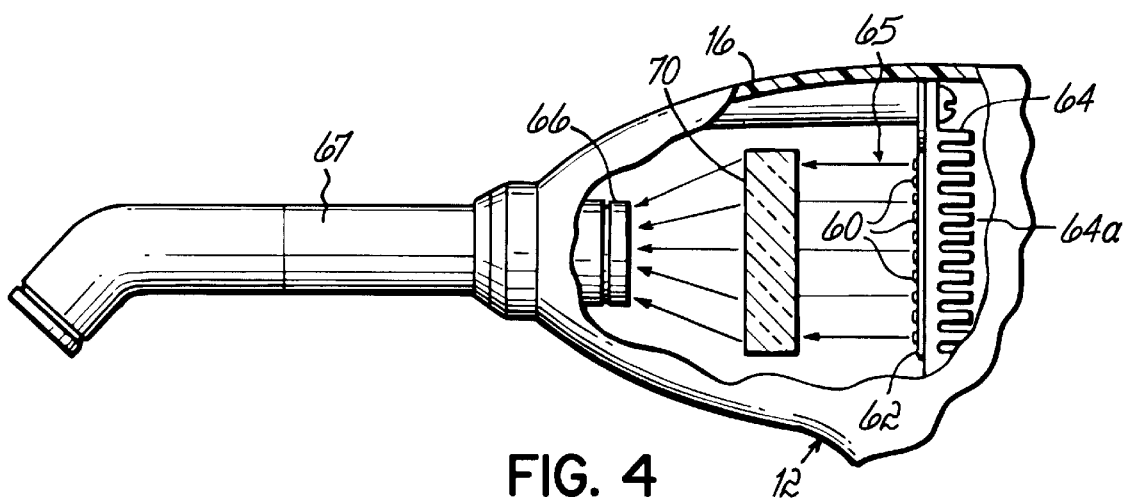
FIG. 4
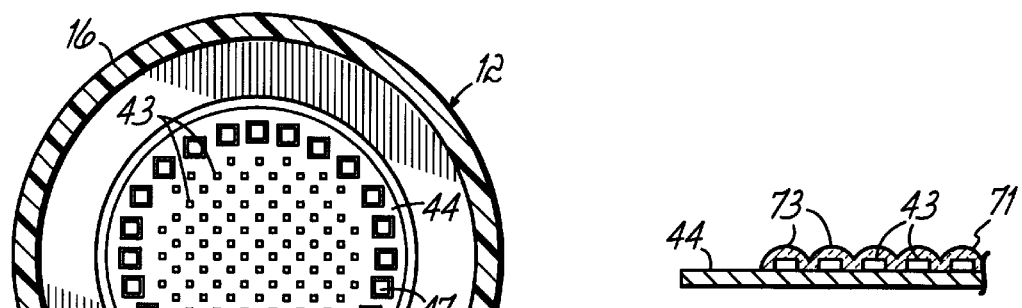
FIG. 3A
FIG. 3
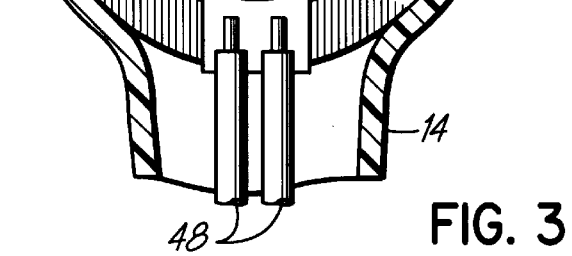
FIG. 5
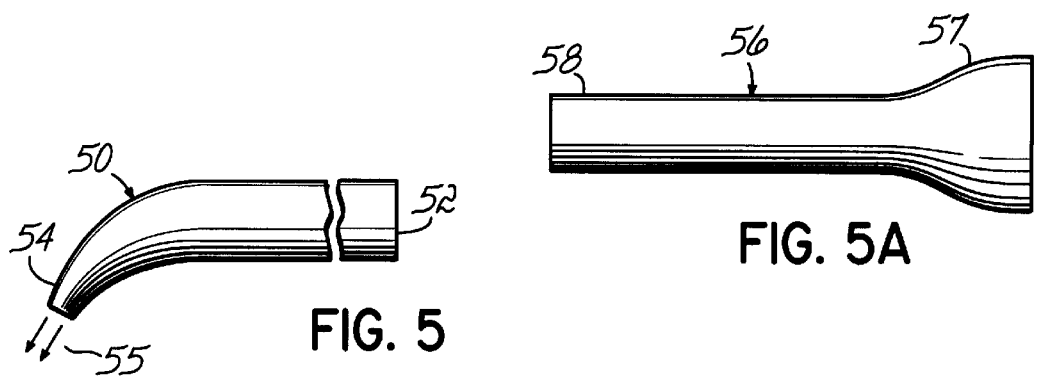
FIG. 5A

APPARATUS AND METHOD FOR CURING MATERIALS WITH RADIATION

FIELD OF THE INVENTION

This application is related to the curing of materials with radiation and, more specifically, to curing dental coating and filling compounds with light.

BACKGROUND OF THE INVENTION

Curable adhesive compounds and bonding or filling compounds are widely used for structurally connecting object surfaces together or for filling gaps or other openings and cavities in an object surface. Such curable compounds are generally manipulated and positioned in a semi-solid state and are then hardened or cured in position to a more solid state. Such curing or hardening is a chemical process which is promoted and driven by one or more curing conditions or factors. For example, the curing process may be the result of exposure of the semi-solid compound and components thereof to air or from exposure of such a compound and its components to an energy source, such as a heat source.

Other curable adhesive and filling compounds are cured by exposure to radiated energy, such as visible light energy. Such compounds, referred to as light-curable compounds, are manipulated in a semi-solid form into or onto the work surface and radiation, preferably in the form of a visible light beam, is directed at a specific wavelength or band of wavelengths onto the compound. The compound includes light-sensitive chemical components therein which, when exposed to the light at the specific wavelength, promote the hardening of the compound in the desired position on the object surface to bond, fill, or coat the surface.

Specifically, light-curable compounds are widely used in dental procedures. Dentists use light-curable dental compounds for coating and sealing tooth surfaces, filling caries and other cavities in the tooth surface, and securing crowns and various other dental structures to a tooth surface. The dental compounds are generally cured by exposure to visible light in the blue range of the spectrum. Once cured, the dental compound reduces further tooth decay, bonds the dental structure, and/or provides additional structure to a tooth.

For curing light-curable dental compounds, visible blue light, and particularly a blue light beam from a hand-held curing light device, is directed onto a tooth surface containing the desired compound layer. The blue light penetrates into the compound layer on the tooth surface for complete curing. The duration of the exposure to blue light for proper curing of the compound layer depends upon the type and thickness of the compound layer, as well as the power and characteristics of the blue light from the curing light device. For example, a thin tooth surface coating or veneer will require less radiated light power, while thicker, deeper fillings for caries and other cavities will require a greater amount of radiated power.

Light-curable compounds have shown very beneficial results in the dental field. However, existing techniques and dental curing light devices utilized to deliver the blue light to the tooth surface have exhibited various drawbacks. For example, it is known that certain wavelengths of blue light are harmful to human tissue. While attempts are made to direct the light beam only on to the tooth surface, a certain amount of oral tissue exposure to the light is inevitable. Therefore, curing light devices for curing dental compounds must have their output radiation limited to within a suitable wavelength band for patient safety. Furthermore, the light-curable compounds are usually sensitive to light having a specific wavelength, such as a blue light wavelength. Therefore, a dental curing light device must be tuned to emit light at the proper wavelengths for patient safety and proper curing.

As a result, current dental curing light devices require special complicated filtering devices or filters which receive broad spectrum light from a lamp element, such as a halogen lamp bulb, and then filter the light to provide only the light at the desirable blue wavelengths. Because of the wide spectrum of radiation delivered by available lamp elements, including visible light, UV light, and infra-red light, prior art curing techniques and light devices have generally been very inefficient. That is, a large amount of the radiated light power is lost due to filtering. For example, the input power to a conventional halogen bulb may typically be around 80 Watts, whereas the output power of light from the dental light device at the desired blue wavelength, for example 400–500 nanometers, is typically less than one-half of a Watt.

Additionally, the efficiency of the prior art dental curing light devices is further degraded by the power loss due to the angle of incidence of the radiated light upon the filtering element. For example, many prior art curing light devices utilize reflective filters which reflect only the desirable blue light onto the tooth surface and dental compound, but transmit light at the undesirable wavelengths to a light absorbing component where it is dissipated. If the angle of incidence of the light from the halogen bulb varies significantly from the desired angle of incidence for the filtering element surface (e.g., 45°), then a reduced amount of the desirable blue light is reflected to the tooth surface. This further decreases the light power which is available for curing the dental compound. Conversely, a higher amount of the undesirable, non-blue light may be reflected onto the tooth surface, rather than being transmitted through the filtering element to be dissipated.

Another drawback with prior art devices is that they require complicated cooling systems to operate within the proper temperature range. The significant amount of light energy at undesirable wavelengths which is generated by the halogen bulb must be filtered or otherwise captured. The captured energy is then dissipated in the form of heat. Therefore, power absorbing and dissipating elements are required within conventional curing light devices. Thermal shields are often utilized in conjunction with reflective filters to absorb and dissipate the unreflected, unused light energy in the form of heat. The high power output required for the halogen bulb to produce the desired blue light power for curing, creates a significantly, high thermal load on the shields. The shields must then be cooled. Generally, fan elements are used in the dental light device to provide such cooling. The additional cooling elements increase the size of the light device and complicate its design. As will be appreciated, it is desirable to keep the light device as small and maneuverable as possible, since it is used in a patient's mouth.

Additionally, a thermal load is placed on the reflective filter element, and it must also be cooled, such as by heat sinks and fans. The absorption devices and heat dissipating systems not only complicate the operation of the light device, but also make it more expensive to produce, and more subject to operational failure.

Another drawback of prior art dental curing light devices is the limited operational life of the lamp element, such as a halogen bulb. The bulbs frequently burn out and must be replaced. Furthermore, the heat generated inside the light device shortens the effective operational lifespan of the bulb.

Attempts have been made in the prior art to address some of these drawbacks. For example, Japanese Patent Applications No. 6-30275, 6-285508, 7-163863, and 8-194786 disclose various devices using solid state semiconductor elements, such as LEDs, to provide a curing light source in the blue range. However, various of these devices require complicated internal designs for focusing of the curing light. Furthermore, as illustrated in the Figures of those applications, the solid state elements utilized would require a somewhat large housing for generating the intensity of light which is necessary for practical use.

Accordingly, it is an objective of the present invention to provide a simple, durable curing light device for hardening or curing light-curable compounds. Particularly, it is an objective to provide such a curing light device for curing dental compounds used for dental fillings and coatings.

It is another objective to provide a curing light which has a compact and simple design which is capable of providing light intensity useful for practical curing applications.

It is still another objective of the present invention to cure compounds with curing light devices utilizing less power and with greater efficiency to reduce the amount of heat energy generated by the device and thus reduce the heat energy which must be dissipated.

It is another objective of the present invention to reduce the operational temperature of a curing light device, thus reducing the need for complicated cooling systems utilized in the prior art.

It is still another objective of the invention to eliminate the necessity of reflective filters and other filter elements within a light device for curing light-curable compounds.

It is still a further objective to provide a blue light device which operates within a small space and is easily manipulated within the mouth of a dental patient.

It is still another objective to increase the effective operational lifespan of the light generating components of a curing light device.

These objectives and various other objectives will become more readily apparent from the Description of the Invention below.

SUMMARY OF THE INVENTION

The present invention addresses the above objectives and provides a durable and efficient curing light device to cure light-curable compounds. The invention is particularly useful for curing dental adhesive and filling compounds with blue light. The device is more energy efficient and generates less heat than prior art devices. Furthermore, a preferred embodiment of the device provides efficient delivery of blue curing light in a simple, durable design and creates new design possibilities for dental curing light devices.

More specifically, one embodiment of the curing light device of the present invention comprises an array of solid state, light-emitting diode dies, each in the form of a small, non-packaged semi-conductor junction mounted on a ceramic substrate or circuit board. The array of non-packaged LED dies collectively are operable for efficiently emitting narrow-band radiation in a small area. In the preferred embodiment of the invention, the LED dies radiate blue light at predominantly a narrow band with a peak wavelength and, most preferably, at a peak blue light wavelength which is suitable for curing dental filling and coating compounds. One desirable blue light wavelength peak for dental applications is approximately 470 nanometers.

The LED dies of the invention are very small and do not have any external plastic packaging. Therefore, a very dense array of die elements is provided by the invention for providing a light beam of practical intensity in a very small space. The dies are surface mounted on a ceramic substrate or circuit board by soldering. The top side of each die is then coupled to the circuit by very thin wires in a microscopic procedure called wire-bonding.

Preferably, the small LED dies, for example 0.3 mm on a side, are arranged on the substrate in a matrix having a circular shape. Preferably, only 0.25 mm$^2$ of substrate space is used for mounting each LED. Generally 200–500 LEDs are used for creating the necessary light power needed for curing available dental compounds. However, a lower number of LEDs may be suitable, and in one embodiment of the invention, 96 LED dies provided suitable power for curing a dental compound.

Since light is radiated generally only at the desired wavelength, the invention eliminates the need for special light filters and reflective elements. Therefore, the invention simplifies the design and operation of the curing light device. Furthermore, the inventive curing light device is more efficient than prior art devices because the power used by the device is predominantly for light at the specific usable blue wavelength rather than for broad spectrum light.

The blue light radiation from the LED array may be captured by a light transmitting device, such as an optical fiber light pipe, and is transmitted and directed through the light pipe and onto the working surface, such as a tooth surface. The light pipe would preferably be a conventional light pipe formed by fusing together a plurality of optical fibers. One embodiment of such a light pipe maintains a uniform diameter along its length. In another embodiment, a focusing light pipe might be utilized which gathers the light from the LED array at one end and transmits the radiation at a smaller or tapered end to further define and concentrate the curing light beam for use on a smaller work surface. The LED dies and light pipe are positioned within a suitably shaped housing which is manually manipulated so that the blue light beam may be directed onto the tooth surface for curing purposes. Alternatively, the array of small dies may be positioned on the tip of a curing device to directly irradiate the dental compound instead of using a light pipe.

A light focusing device, such as an optical lens, may be utilized between the array of LED dies and the light pipe for further focusing and directing the light into the light pipe for more efficient transmission onto the tooth surface. Preferably, the lens is a converging-type lens which focuses the light from the LED array into the small light pipe end. As an alternative to a single large lens, the array of dies may be coated or encapsulated in plastic so that individual micro lenses are formed around each of the dies for focusing the light therefrom.

A DC power supply provides power of up to 50 Watts for driving the LED die array. The array generates some heat, and therefore, is mounted on a simple heat sink, which may be utilized with or without a forced air device, such as a fan, to further dissipate the heat. While some heat is generated, the array of surface-mounted LEDs of the inventive curing light device generates substantially less heat than conventional dental curing lights. Furthermore, the elimination of reflective filtering elements and thermal shields further reduces the heat and thermal stresses which are generated by prior art devices.

In another embodiment of the invention, surface mounted LEDs are utilized. The surface mounted LEDs are larger than the LED dies discussed above, and thus will take up more space in an array. The surface-mounted LEDs are preferably arranged in a circular pattern, similar to the LED dies, for a circular light pattern. The array of LEDs is soldered to an appropriate mounting base, such as a printed circuit board. The surface-mounted LED array preferably utilizes a separate lens for focusing the irradiated light.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

FIG. 1 is a side view in partial cross-section of a curing light device utilizing traditional packaged LEDs.

FIG. 2 is a side view in partial cross-section of one embodiment of the invention.

FIG. 3 is a cross-sectional view taken on lines 3—3 of FIG. 2 of an array of light-emitting dies mounted on a substrate.

FIG. 3A is a cross-sectional view of an alternative embodiment of the present invention.

FIG. 4 is a side view in partial cross-section of an alternative embodiment of the present invention.

FIGS. 5 and 5A are side views of alternative embodiments of a light pipe for use in the invention.

DETAILED DESCRIPTION OF THE INVENTION

Figure 1A:
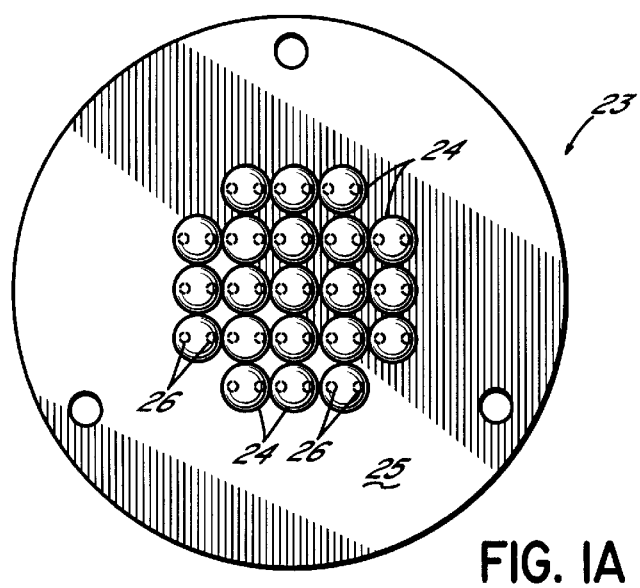
FIG. 1A is a plan view of an alternative LED array as shown in FIG. 1.

FIG. 1 illustrates a curing light device for curing light-curable compounds such as dental compounds. Such a device utilizes blue light LEDs such as those available from Panasonic, Model No. LNG997CKB.

In FIG. 1, device 10 includes a generally gun-shaped plastic housing 12 which includes a handle portion 14 and a barrel portion 16. The operator, such as a dentist, grips housing 12 at the handle portion 14 and directs the barrel portion 16 in the direction of the tooth surface and compound to be cured (not shown). For curing dental filling and coating compounds, the dentist would generally direct the barrel portion into the mouth of a patient. The handle portion 14 includes an operational trigger switch 18 which is operably coupled to a power supply 20 within the barrel portion for selectively supplying power to light-emitting elements 32 to generate a curing light beam, as discussed below.

Barrel portion 16 supports a light transmitting device, such as a light pipe 22, which is appropriately formed and angled to direct the curing light onto a tooth surface or other work surface. It will be understood by a person of ordinary skill in the art that the shape of housing 12 may vary. Barrel portion 16 is shown as solid; however, it might also be vented for heat dissipation purposes as discussed further hereinbelow. The light pipe 22 is preferably removably secured in the end of barrel portion 16 by any suitable method as is known in the art. For example, the light pipe 22 might be screwed into and out of the barrel portion 16. The housing body 12 is formed of a suitable light-weight plastic material such as polysulphone.

The DC power supply 20 of device 10 is coupled to a conventional base AC source 15, such as through a cord 13 as is conventional with dental curing light devices. The base AC source 15 is mounted within a base structure (not shown) for the device which includes conventional controls for the light device 10, such as a timer for timing the operational radiation cycle for the device when the trigger switch 18 is engaged.

The narrow wavelength band of radiation or light is generated by an array 30 of conventional light-emitting diodes 32. Preferably, a single wavelength of light is generated, but a narrow wavelength band comprising the single wavelength peak desired would also be suitable. The array 30 creates a field or beam of light 34, a portion of which is captured by a receiving end 35 of the light pipe 22. The light beam 34 is transmitted through light pipe 22 as a more narrow beam 36 and is emitted at a transmission end 37 of the light pipe 22 onto a work surface or tooth surface (not shown).

In one prototype tested during development of the invention, the inventors utilized nine high-intensity, blue light LEDs 32 which had integral lenses therein which produced a 15 degree radiation or viewing angle. Again, suitable LEDs are commercially available from Nichia or Panasonic under Model No. LNG997CKB. The LEDs are considered as blue light LEDs because they generate light at a wavelength of approximately 470 nm, which is blue within the visible light spectrum. Other blue light wavelengths might also be utilized, depending upon the particular curing characteristics of the light-curable compound.

The LEDs 32 of the embodiment in FIG. 1 are mounted on a suitable base 40, such as G10 (circuit board material), and are arranged in a 3×3 matrix. Each of the LEDs 32 is adjusted individually on the base 40 to concentrate the beam into the receiving end of the light pipe 22. For example, as illustrated in FIG. 1, some of the LEDs on the outer edges of the array are bent at their electrical leads 33 toward the center of the array to focus the light 34. The LEDs 32 are electrically coupled to DC power supply 20. A cooling fan indicated by reference numeral 42 is utilized to surface cool the LEDs 32 and is also powered by supply 20.

In testing the prototype shown in FIG. 1, the DC current through the LEDs was increased in several gradations and radiated light energy measurements were taken with a laser power monitor instrument (not shown). The curing ability of the LEDs 32 was checked by using one millimeter thick slices of a light-curable dental compound, such as *Kerr Dentin XRV Herculite*, which were placed proximate the transmission end 36 of light pipe 22. At DC current levels of approximately 65 mA, a radiated power level of approximately 30 mW from beam 36 was measured. The dental compound slices were radiated for approximately one minute. Through such experimentation, it was determined that the compound was successfully cured, at least partially. Longer curing times and higher radiation power levels may be necessary for a full cure, depending upon the thickness of the compound.

Currently, a number of LED manufacturers, including Panasonic, have made available blue light LEDs which include semiconductor junctions doped with Silicon Carbide to provide a generally narrow band wavelength light output. A plurality or array of such devices was utilized in the test prototype because they have a relatively low individual power rating, as compared to halogen lamp bulbs.

A fan element 42 was utilized in the test prototype shown in FIG. 1, although the lack of filtering devices reduces the heat dissipation requirements of curing light device 10. Since the radiation 34 from the LEDs 32 is generally a single wavelength, or a very narrow band of wavelengths, energy from the unwanted wavelengths of visible light does not have to be dissipated in the form of heat. Therefore, fan element 42 could be eliminated in an alternative test prototype.

FIG. 1A illustrates another test prototype LED array for use, such as in the device of FIG. 1. Array 23 utilizes individual LEDs 24 having a relatively standard 3.0 mm diameter size. Twenty-one (21) LEDs are shown mounted to base 25 by the wire leads 26 similar to the array in FIG. 1. Base 25 is a printed circuit board material such as G10. The LEDs used in the test array 23 are Panasonic No. LNG997CKB, and the light therefrom was focused to a 15% viewing area into a light pipe similar to that shown in FIG. 5A. The circular array 23 of LEDs ensures good transmission into a light pipe. Preferably, a cooling fan, as shown in FIG. 1, is used to cool array 23.

The array 23 was tested and it was determined that a driving current of approximately 50 mA per LED 24 is optimal. At that current, the array produced an output power of approximately 40 mW. Measuring the output, it was found that the transmission percentage, or relative intensity, for the light array at around 470 nm increases as the drive current increases between 30 mA and 60 mA.

While the arrays as illustrated in FIGS. 1 and 1A are sufficient for curing, at least partially, dental compound materials, they are still somewhat large and bulky, generate a relatively substantial amount of heat, and require separate focusing apparatuses. Therefore, there is still a need for a suitable, compact dental curing device which is efficient, durable, relatively cool, and can provide a density of light generating elements in a small package which will generate a curing beam of suitable intensity.

In accordance with the principles of the present invention, FIG. 2 illustrates an embodiment of the present invention in which a plurality of LED dies are utilized to generate the curing radiation. More specifically, a plurality of LED dies 43 are mounted on a ceramic substrate 44, such as by soldering. The ceramic substrate, such as alumina, is utilized for providing the necessary cooling of the elements 43 as they operate. The substrate 44, in turn, is mounted on a heat sink device 46, having cooling fins 46a, for further cooling purposes. A forced air element (not shown), such as the fan element 42 in FIG. 1, might be utilized for directing or forcing air toward fins 46a and over the heat sink 46 to provide further cooling.

The LED dies of the invention are made of light-generating semiconductor material which is not packaged or otherwise covered in plastic. That is, the LED dies of the invention are essentially unpackaged semiconductor junctions for generating the desired light. Therefore, the dies are very small and substantially smaller than conventional LEDs used in the test prototype of FIGS. 1 and 1A.

Referring to FIG. 3, the dies 43 are mounted in an array as shown on the generally circular ceramic substrate 44. Suitable power lines 48 coupled to a DC power supply 20 provide the necessary power for illuminating the devices 43. The individual dies or chips 43 are generally rectangular in shape and measure approximately 0.3 mm (0.012 inches) on a side, or 0.09 mm$^2$ in area. Therefore, the area needed in the array for a single die is substantially smaller than the area needed in the array for a conventional LED. The LEDs are mounted side-by-side in a matrix for forming a beam of light. The matrix or array arrangement of the devices 43 is in a circular shape to correspond to the circular shape of ceramic element 44 and the cross-section of barrel portion 16, which is circular. Furthermore, the circular array of FIG. 3 generates a generally circular beam of light. Other substrate shapes may be used, depending upon the design of device 10. It has been determined that each LED die 43 should have approximately 0.5 mm per side, or approximately 0.25 mm$^2$ of ceramic substrate space for proper mounting, operation, and cooling purposes.

Metal tracks (not shown) are formed on the ceramic substrate and the dies 43 are appropriately soldered to the tracks on a bottom side. The top sides of the dies 43, shown in the view of FIG. 3, are coupled to conductive pads by very thin wires (not shown) in a microscopic procedure referred to as wire bonding. The conductive pads 47, in turn, are coupled to leads 48.

In the embodiments illustrated in FIGS. 2, 3, and 4, 96 LEDs are arranged as shown for providing the necessary curing radiation. Each LED 43 requires approximately 4–5 Volts of DC bias, and are preferably biased in series circuits of four LEDs, for a total of approximately 20 volts DC required per series circuit. The 96 LEDs are thus arranged as 24 series circuits of four LEDs each on substrate 44. It is important to keep the density of the light beam to a maximum. The LED devices therefore need to be laid out to avoid any blank spots in the beam. The array of 96 LEDs in the arrangement of FIG. 3 requires a circular area of approximately 8 mm$^2$ or 0.3125 inches in diameter.

The dies 43 of the invention provide a very high density array which provides suitable curing power in a small area. As discussed, a very large number of individual dies 43 may be mounted in a small area. Suitable dies for the invention are available from CREE Research, Inc., of Durham, N.C. as Part No. C430-DH85.

Referring to FIG. 3, each 4 LED series circuit is coupled to the DC power supply 20 through wire leads 48 and conductive pads 47 which are arranged around the periphery of substrate 44.

It should be appreciated that the spacing of the individual LEDs 43 in the array may be varied as necessary depending upon the size of substrate 44, the cooling requirements, and the cooling system available. Furthermore, the number of LEDs utilized and the electrical wiring scheme may also vary from that shown in the drawings without departing from the scope of the invention.

An array of 96 surface-mounted blue LEDs arranged as shown in FIG. 3 generated 480 nm blue light at a radiated power level of approximately 30 mW. While the embodiment illustrated in FIG. 2 utilizing 96 LEDs is suitable for some curing applications, a greater number of LEDs may be necessary for generating the required power for a wide range of curing conditions. For example, deeper fillings or thicker surface coatings may require additional power. Radiated power levels of approximately 200 mW/cm$^2$ or greater are generally necessary for curing the available dental compounds. Other intensities may be necessary for curing other light-sensitive compounds.

To that end, it is anticipated that the number of elements in the array will be determined by the intensity of the individual dies. A number of dies in the range of 200–500 elements might be used. Elements having the shape and dimensions as discussed above would require approximately 1.25 cm$^2$ for approximately 500 LEDs. Arranged in a circular shape, as illustrated in FIG. 3, such an array would be approximately 18 mm (0.7 inches) in diameter. Of course, such size dimensions will vary depending upon the number of elements used as well as heat dissipation considerations and electrical connections and biasing of the elements.

The invention provides many advantages over the prior art dental compound curing technology. One particular advantage is that the dies 43 are solid state devices which have virtually an unlimited life. Furthermore, the radiation or light output from the dies is not degraded toward the end of the useful life of the devices, as generally occurs with the halogen lamp bulbs used in the prior art. Therefore, even up to ultimate failure of the dies, they will provide suitable radiation for curing purposes. The dies 43 further eliminate the need for specific filtering of the undesired wavelengths of broad-spectrum light which is required with prior art halogen lamp bulbs. The dies 43 preferably provide radiation at a desirable blue light wavelength, for example, 470 nm, or at a desirable blue light band of wavelengths.

Referring again to FIG. 2, the LED dies 43 preferably are arranged so that as much as possible of the radiation is directed into the receiving end 35 of light pipe 22. The dies 43 are preferably positioned as close to the receiving end 35 of the light pipe 22 as possible to eliminate, or at least minimize, any loss of radiation.

Light pipes or light guides 22 may be commercially available and come in a variety of different sizes; for example in diameters of 8 mm, 11 mm and 13 mm. Generally, such light pipes are formed of a plurality of optical fibers (for example, approximately 5,000 fibers) which are fused together into a single light pipe structure. The light transmitted into the receiving end 35 is then transmitted through the light pipe and is directed out the transmission end 37 as a narrow beam of radiation 36. In the embodiment of FIG. 1, the light pipe maintains a uniform diameter from the receiving end 35 to the transmission end 37. At the transmission end 37, the light pipe is bent or curved for directing beam 36 in a downward direction onto the work surface, such as a tooth surface. The light pipe 22 is also preferably rotatable in the barrel portion 16 of housing 12 so as to direct the beam 36 in other directions, as necessary with respect to housing 12.

In an alternative embodiment of the invention, as illustrated in FIG. 5, a tapered light pipe 50 might be utilized which has a larger diameter receiving end 52 (e.g. 13 mm) which tapers down to a smaller diameter transmission end 54 (e.g. 6–7 mm). In that way, the light captured in the receiving end 52 is directed to form a more focused or narrow beam 55. FIG. 5A shows another suitable version of a tapered light pipe. Light pipe 56 has a wide receiving end 57 which tapers to a smaller diameter and transmission end 58.

FIG. 4 illustrates an alternative embodiment of the invention which utilizes a focusing device 70 which might be utilized when the array of dies 60 generates a beam 65 substantially wider than the receiving end 66 of a light pipe 67. More specifically, the array of dies 60 is mounted on substrate 62, which is appropriately coupled to a heat sink element 64 having fins 64a, and may generate a beam of radiation 65 which is broader or wider than the receiving end 66 of light pipe 67. For efficient transfer of the radiation to the light pipe 67 and to prevent a portion of the radiation 65 from being lost, a radiation focusing device 70, such as an optical lens, may be utilized. Lens 70 is preferably a converging optical lens which focuses the radiation 65 from the dies to a smaller size beam as shown in FIG. 4 for efficient transmission into the receiving end 66 of light pipe 67. In that way, a large percentage of the radiation generated by the elements 60 is received by the light pipe and transmitted thereby for curing purposes. The embodiment illustrated in FIG. 4 utilizes the heat sink 64 for dissipation of heat generated by the array of elements 60. A forced air device (not shown) might also be utilized in conjunction with the heat sink 64 for heat dissipation purposes.

The embodiment illustrated in FIG. 2 does not utilize a focusing device such as a lens. However, in accordance with the principles of the present invention, a microlens might be formed over each die to focus the light generated therefrom. The microlenses over the individual dies would be an alternative to the large lens 70 illustrated in FIG. 4. To that end, referring to FIG. 3A, the entire array of dies 43 can be encapsulated in a continuous layer of clear plastic 71. The layer 71 is formed to create individual curved microlenses 73 over each of the individual dies. The microlenses focus the emitted light toward the fiber optic light guide for more efficient transmission of the blue light. Alternatively, individual layers and microlenses might be formed separately over the dies 43 rather than as part of a one large continuous layer.

Figure 6:
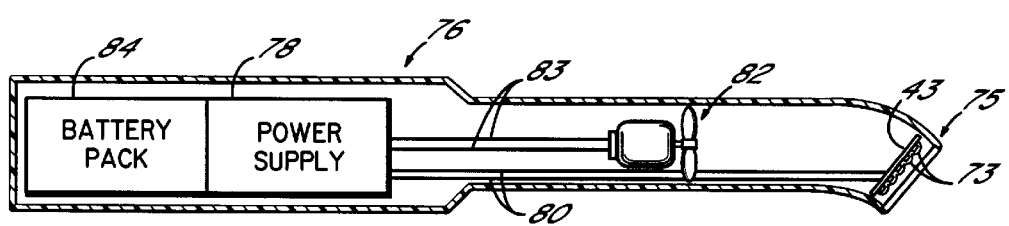
FIG. 6 is a cross-sectional view of an alternative embodiment of the present invention.

The use of an array of microlenses 73 will eliminate the need for a larger single lens 70 and thus will produce an even more compact design for the inventive light curing device. Referring to FIG. 6, the array of dies 43, which produces a sufficient intensity and is properly focused using microlenses 73, could be positioned at the tip 75 of the light curing device 76. Such a design would eliminate the need for a light pipe and would thus eliminate any loss of power associated with a light pipe. The array of dies 43 would directly illuminate a tooth or dental compound. As shown in FIG. 6, the die array is coupled to a power supply 78 by lines 80. If necessary, a small fan unit 82 might be utilized for cooling purposes. Fan unit 82 is also coupled to power supply 78 by lines 83.

Therefore, depending on the intensity of the individual dies, the number of dies in the array is minimized in accordance with the principles of the invention. In the embodiment illustrated in FIG. 6, a very small power supply 78 may be utilized to drive the minimized number of dies. A small rechargeable battery pack 84 may be used. The inventive light could therefore be made as small as a fountain pen, similar to the embodiment shown in FIG. 6.

Figure 7:
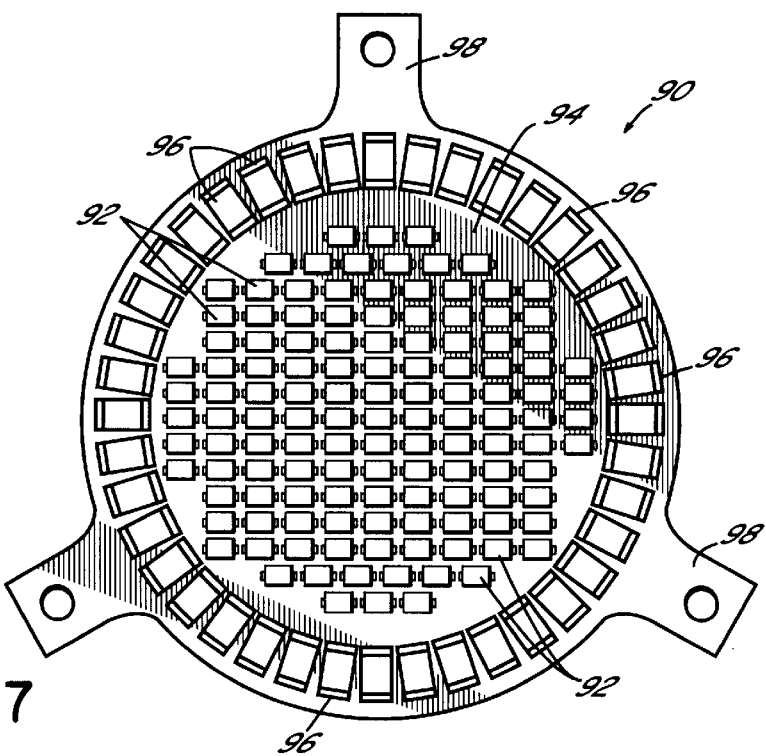
FIG. 7 is a plan view of an alternative array of LEDs utilized in accordance with the principles of the present invention.

FIG. 7 shows an alternative embodiment of the present invention which utilizes small packaged surface mountable LEDs in an array for generating the blue light of the invention. Array 90 is generally circular in shape and includes a plurality of surface-mounted LEDs 92 which are mounted on a base 94 of printed circuit board material, such as G10. The surface-mounted LEDs are commercially available from Nichia and have a generally rectangular surface area on the base 94 of approximately 0.050×0.065 inches. Therefore, the surface-mounted LEDs 92 are larger than the dies illustrated in FIGS. 2–4, and would require a larger surface area for the same number of elements in an array. The LEDs 92 are electrically connected in series of 3 LEDs which are coupled to an appropriate power supply through resistors 96 positioned around the periphery of base 94. Attachment flanges 98 are used to secure base 94 within a curing light device. While the surface-mounted embodiment will be larger, on average, than the embodiments using dies, such an array will still be smaller than one using conventional, bulky LEDs having large packages and long wire leads. While 126 LEDs are shown in FIG. 7, larger or smaller array sizes might be utilized.

Thus the present invention provides a small, compact and durable curing device for hardening or curing light-curable materials such dental filling and coating compounds. Because light is generated in a narrow wavelength band of the spectrum, and preferably as close to a single blue light wavelength as possible, reflective filters and other filtering elements are not required within the inventive device for filtering and removing unused radiation generated by the traditional lamp bulbs. Therefore, the inventive device significantly reduces the heat generated within the curing device and eliminates the need for complicated cooling systems. Furthermore, the power efficiency of the device is increased because most if not all of the radiation generated is usable for the purposes of curing. The small size of the radiating dies and surface-mounted LEDs, as well as the elimination of filters and complicated heat dissipation mechanisms provides a curing device which may be assembled in a housing substantially smaller than conventionally available. Accordingly, the device would be lighter and easier to manipulate for the operator, such as a dentist. Still further, the useful life of the device is increased because of the solid state nature of the dies and surface-mounted LEDs. Furthermore, there will be no degradation in the radiation output toward the end of the useful life of the elements as generally occurs with halogen lamps. As such, the invention provides a variety of new design possibilities for curing devices, and particularly for dental curing devices.

While the present invention has been illustrated by the description of the embodiments thereof, and while the embodiments have been described in considerable detail, it is not the intention of the applicant to restrict or in any way limit the scope of the appended claims to such detail. Additional advantages and modifications will readily appear to those skilled in the art. Therefore, the invention in its broader aspects is not limited to the specific details representative apparatus and method, and illustrative examples shown and described. Accordingly, departures may be made from such details without departure from the spirit or scope of applicant's general inventive concept.

What is claimed is:

1. An assembly for dental work in the mouth of a patient comprising:
    a light-curable dental compound adapted to be located in the mouth of a patient, the compound being curable with light of a specified wavelength;
    a hand-held dental instrument including a housing with an operator grippable section and a light emitting section, the light emitting section configured for being positionable within the mouth of a patient proximate the light-curable compound;
    a plurality of individual solid state, unpackaged, light-emitting dies, the dies being individually mounted on a substrate supported by the housing to form a collective array on said substrate in the housing, the individual dies each being a semiconductor junction free of an integral package and lens, the array of dies operable for collectively emitting light having wavelengths within a narrow band of wavelengths, said narrow band of wavelengths including said specified wavelength at which the light-curable dental compound is curable;
    said substrate having electrically conductive elements positioned thereon, said individual dies each being electrically coupled to at least one of said elements for coupling to a power supply to illuminate the dies;
    a heat sink coupled to the substrate for dissipating heat from the array;
    a forced air device for directing air to the heat sink for further heat dissipation;
    a light transmitting device for capturing said light from the array of dies and transmitting a beam of the light out of the housing to the dental compound;
    whereby the beam may be used to cure the light-curable dental compound in the mouth of a patient.

2. The assembly of claim 1 wherein said solid narrow wavelength band includes a blue light wavelength.

3. The assembly of claim 1 wherein said narrow wavelength band includes a wavelength of approximately 470 nanometers.

4. The assembly of claim 1 wherein said light transmitting device comprises at least one fiber optic element.

5. The assembly of claim 1 wherein said light transmitting device comprises a plurality of fiber optic elements operably coupled together for directing said beam.

6. The assembly of claim 1 further comprising an optical focusing device for focusing said light before it is captured by said light transmitting device.

7. The assembly of claim 6 wherein said optical focusing device comprises an optical lens.

8. The assembly of claim 1 wherein said light transmitting device has a receiving end and a transmission end, the transmission end being dimensioned smaller than said receiving end for narrowing the light beam captured by said light transmitting device.

9. The assembly of claim 1 wherein said dies are mounted on a ceramic substrate.

10. The assembly of claim 9 wherein said narrow spectrum radiation comprises predominantly a single wavelength.

11. The assembly of claim 10 wherein said single wavelength radiation is blue radiation.

12. The assembly of claim 1 further comprising a layer positioned over at least one of said dies, the layer forming a microlens over said at least one die to focus light generated by said at least one die.

13. A method for curing light-curable dental compounds in the mouth of a patient comprising:
    positioning a light-curable dental compound in the mouth of a patient which is curable with light of a specified wavelength;
    generating light having wavelengths within a narrow band of wavelengths using a plurality of individual solid state, unpackaged light-emitting dies, the dies being individually mounted on a substrate to form a collective array on said substrate, the individual dies each being a semiconductor junction free of an integral package and lens and collectively generating light wherein the narrow band of wavelengths includes said specified wavelength;
    coupling a heat sink to the substrate and directing air onto the heat sink for dissipation of heat from the array of dies;
    capturing said light with a light transmitting device and transmitting a beam of the light;
    directing the light beam onto the light-curable compound in the mouth of a patient for curing the compound.

14. The method of claim 13 wherein said narrow wavelength band includes a blue light wavelength.

15. The method of claim 13 wherein said narrow wavelength band includes a wavelength of approximately 470 nanometers.

16. The method of claim 13 wherein said light is captured with at least one fiber optic element.

17. The method of claim 13 wherein said light is captured with a plurality of fiber optic elements operably coupled together for transmitting said light as a beam.

18. The method of claim 13 further comprising focusing said light before it is transmitted.

19. The method of claim 18 wherein said focusing of the light is accomplished with an optical lens.

20. The method of claim 13 further comprising mounting said dies onto a ceramic substrate to form said array.

21. The method of claim 13 further comprising positioning a layer of material over at least one of said dies in the array to form a microlens over said at least one die.

22. The method of claim 13 further comprising shaping said array to generally correspond to the shape of an end of the light transmitting device.

23. An assembly for dental work in the mouth of a patient comprising:

a light-curable dental compound adapted to be located in the mouth of a patient which is curable with light of a specified wavelength;

a hand-held dental instrument including a housing with an operator grippable section and a light emitting section, the light emitting section including a forwardmost tip section configured for being positionable within the mouth proximate the light-curable compound;

a plurality of individual solid state, unpackaged, light-emitting dies, the dies being individually mounted on a substrate to form a collective array on said substrate, the individual dies each being a semiconductor junction free of an integral package and lens, the array of dies operable for collectively emitting light having wavelengths within a narrow band of wavelengths, said narrow band of wavelengths including said specified wavelength at which the light-curable dental compound is curable;

the array of dies being positioned at the tip section of said housing for being positioned in a patient's mouth for directly emitting light from the array of individual dies onto said dental compound to cure the compound;

whereby the light more directly cures the light-curable dental compound in the mouth of a patient.

24. The assembly of claim 23 further comprising a rechargable power supply coupled to the array of dies to power the dies.

* * * * *